(12) United States Patent
Beerens et al.

(10) Patent No.: US 10,265,174 B2
(45) Date of Patent: Apr. 23, 2019

(54) IMPLANT WITH SUTURE ANCHORS AND METHOD

(71) Applicant: XILLOC MEDICAL B.V, Maastricht (NL)

(72) Inventors: Maikel Beerens, Maastricht (NL); Erik Boelen, Ittervoort (NL)

(73) Assignee: XILLOC MEDICAL B.V., Maastricht (NL)

( * ) Notice: Subject to any disclaimer, the term of this patent is extended or adjusted under 35 U.S.C. 154(b) by 0 days.

(21) Appl. No.: 15/328,775

(22) PCT Filed: Jul. 17, 2015

(86) PCT No.: PCT/EP2015/066468
§ 371 (c)(1),
(2) Date: Jan. 24, 2017

(87) PCT Pub. No.: WO2016/012376
PCT Pub. Date: Jan. 28, 2016

(65) Prior Publication Data
US 2017/0209274 A1  Jul. 27, 2017

(30) Foreign Application Priority Data
Jul. 24, 2014  (EP) ..................................... 14178351

(51) Int. Cl.
*A61F 2/28* (2006.01)
*A61B 17/68* (2006.01)
(Continued)

(52) U.S. Cl.
CPC .......... *A61F 2/2875* (2013.01); *A61B 17/688* (2013.01); *A61B 17/8061* (2013.01);
(Continued)

(58) Field of Classification Search
CPC ...... A61F 2/28; A61F 2/2875; A61F 2/30749; A61B 2017/0404; A61B 2017/0414;
(Continued)

(56) References Cited

U.S. PATENT DOCUMENTS

| 4,388,921 A | 6/1983 | Sutter et al. |
| 5,201,737 A | 4/1993 | Leibinger et al. |

(Continued)

FOREIGN PATENT DOCUMENTS

| DE | 10205912 A1 | 8/2003 |
| EP | 1099416 A2 | 5/2001 |

(Continued)

OTHER PUBLICATIONS

International Search Report and Written Opinion for International patent application No. PCT/EP2015/066468, dated Sep. 25, 2015.

(Continued)

*Primary Examiner* — Alvin Stewart
(74) *Attorney, Agent, or Firm* — Steven M. Koehler; Westman, Champlin & Koehler, P.A.

(57) ABSTRACT

An implant comprises a U-shaped suture channel which extends along a center line which has first and second end openings opposite each other opening to a common face. In an aspect the suture channel has a middle portion with a first size in cross section with respect to the center line of the suture channel and at least one of the end openings has a second size in cross section larger than the first size. In another aspect the first and second end openings of the U-shaped suture channel are formed by a first hole and a second hole extending into the implant from the common face in respective first and second directions extending into the implant from the common face, the first hole and the second hole communicating within the implant and provid- (Continued)

ing the U-shaped suture channel through the implant, for guiding curved suture needles through the suture channel.

19 Claims, 7 Drawing Sheets

(51) Int. Cl.
  *A61B 17/80* (2006.01)
  *A61F 2/30* (2006.01)
  *A61B 17/04* (2006.01)
  *A61B 17/56* (2006.01)
(52) U.S. Cl.
  CPC ...... *A61F 2/30749* (2013.01); *A61F 2/30942* (2013.01); *A61B 17/0401* (2013.01); *A61B 17/8085* (2013.01); *A61B 2017/568* (2013.01); *A61F 2002/3096* (2013.01); *A61F 2002/30784* (2013.01)
(58) Field of Classification Search
  CPC .... A61B 2017/0438; A61B 2017/0445; A61B 2017/0458; A61B 17/688; A61B 17/8061; A61B 17/8085
  See application file for complete search history.

(56) References Cited

U.S. PATENT DOCUMENTS

| | | |
|---|---|---|
| 5,501,685 A | 3/1996 | Spetzler |
| 5,569,250 A | 10/1996 | Sarver et al. |
| 5,669,912 A | 9/1997 | Spetzler |
| 6,063,106 A * | 5/2000 | Gibson .............. A61B 17/0401 24/115 R |
| 6,149,653 A | 11/2000 | Deslauriers |
| RE37,249 E | 1/2001 | Leibinger et al. |
| 6,174,324 B1 * | 1/2001 | Egan ................. A61B 17/0487 156/73.1 |
| 6,179,839 B1 | 1/2001 | Weiss et al. |
| 6,197,030 B1 | 3/2001 | Pham |
| 6,379,363 B1 | 4/2002 | Herrington et al. |
| 6,537,277 B2 | 3/2003 | Vom Berg et al. |
| 6,618,623 B1 | 9/2003 | Pless et al. |
| 7,189,237 B2 | 3/2007 | Huebner |
| 7,604,657 B2 * | 10/2009 | Orbay ................ A61B 17/8061 606/280 |
| 8,267,973 B2 | 9/2012 | Humphrey |
| 8,469,999 B2 | 6/2013 | Gonzalez-Hernandez |
| 8,535,313 B1 | 9/2013 | Masson |
| 8,579,944 B2 | 11/2013 | Holloway |
| 8,652,170 B2 | 2/2014 | Leung |
| 9,307,979 B1 * | 4/2016 | Bennett ............ A61B 17/06166 |
| 9,314,236 B2 * | 4/2016 | Graf ................... A61B 17/0401 |
| 2002/0161439 A1 * | 10/2002 | Strobel .............. A61B 17/0401 623/13.14 |
| 2004/0044406 A1 * | 3/2004 | Woolfson ............. A61F 2/2409 623/2.11 |
| 2004/0254593 A1 | 12/2004 | Fallin |
| 2005/0171544 A1 | 8/2005 | Falkner, Jr. |
| 2005/0288709 A1 | 12/2005 | Fallin |
| 2006/0189987 A1 * | 8/2006 | Orbay ................ A61B 17/1721 606/62 |
| 2006/0224242 A1 | 10/2006 | Swords et al. |
| 2006/0276896 A1 | 12/2006 | Fallin |
| 2007/0093835 A1 * | 4/2007 | Orbay ................ A61B 17/8061 606/291 |
| 2007/0135816 A1 * | 6/2007 | Kropf ................ A61B 17/0401 606/326 |
| 2007/0233241 A1 * | 10/2007 | Graf ................... A61B 17/0401 623/13.14 |
| 2009/0287215 A1 | 11/2009 | Fisher |
| 2010/0125297 A1 * | 5/2010 | Guederian ......... A61B 17/0401 606/232 |
| 2010/0222812 A1 * | 9/2010 | Stone ................ A61B 17/0401 606/232 |
| 2010/0249930 A1 * | 9/2010 | Myers ............... A61B 17/0401 623/13.14 |
| 2011/0144699 A1 | 6/2011 | Fallin |
| 2012/0046747 A1 * | 2/2012 | Justin ................ A61B 17/0401 623/13.14 |
| 2012/0059469 A1 * | 3/2012 | Myers ............... A61B 17/0401 623/13.14 |
| 2013/0116695 A1 | 5/2013 | Fisher |
| 2014/0005729 A1 | 1/2014 | Dimatteo |
| 2014/0052176 A1 | 2/2014 | Conley |
| 2015/0094762 A1 * | 4/2015 | Spenciner ............ A61F 2/0811 606/232 |
| 2015/0157314 A1 | 6/2015 | Dimatteo |
| 2015/0173813 A1 | 6/2015 | Larabeth |
| 2017/0273776 A1 * | 9/2017 | Kam .................. A61B 17/0401 |

FOREIGN PATENT DOCUMENTS

| | | |
|---|---|---|
| EP | 2014258 A1 | 1/2009 |
| EP | 2480170 B1 | 4/2014 |
| GB | 2379185 A | 3/2003 |
| WO | 9747246 A1 | 12/1997 |
| WO | 0074578 A2 | 12/2000 |
| WO | 2005074580 A2 | 8/2005 |
| WO | 2006130596 A2 | 12/2006 |
| WO | 2012047925 A2 | 4/2012 |
| WO | 2014028864 A1 | 2/2014 |

OTHER PUBLICATIONS

State Intellectual Property Office of The People's Republic of China in corresponding Chinese Application No. 201080050794.2, dated Mar. 4, 2014.
International Search Report, dated Jan. 21, 2011 in connection with International Patent Application No. PCT/EP2010/063887.
Dr. Gabrielle Kiss, "3D print technology replaces a skull in the United States", Mar. 7, 2013.

* cited by examiner

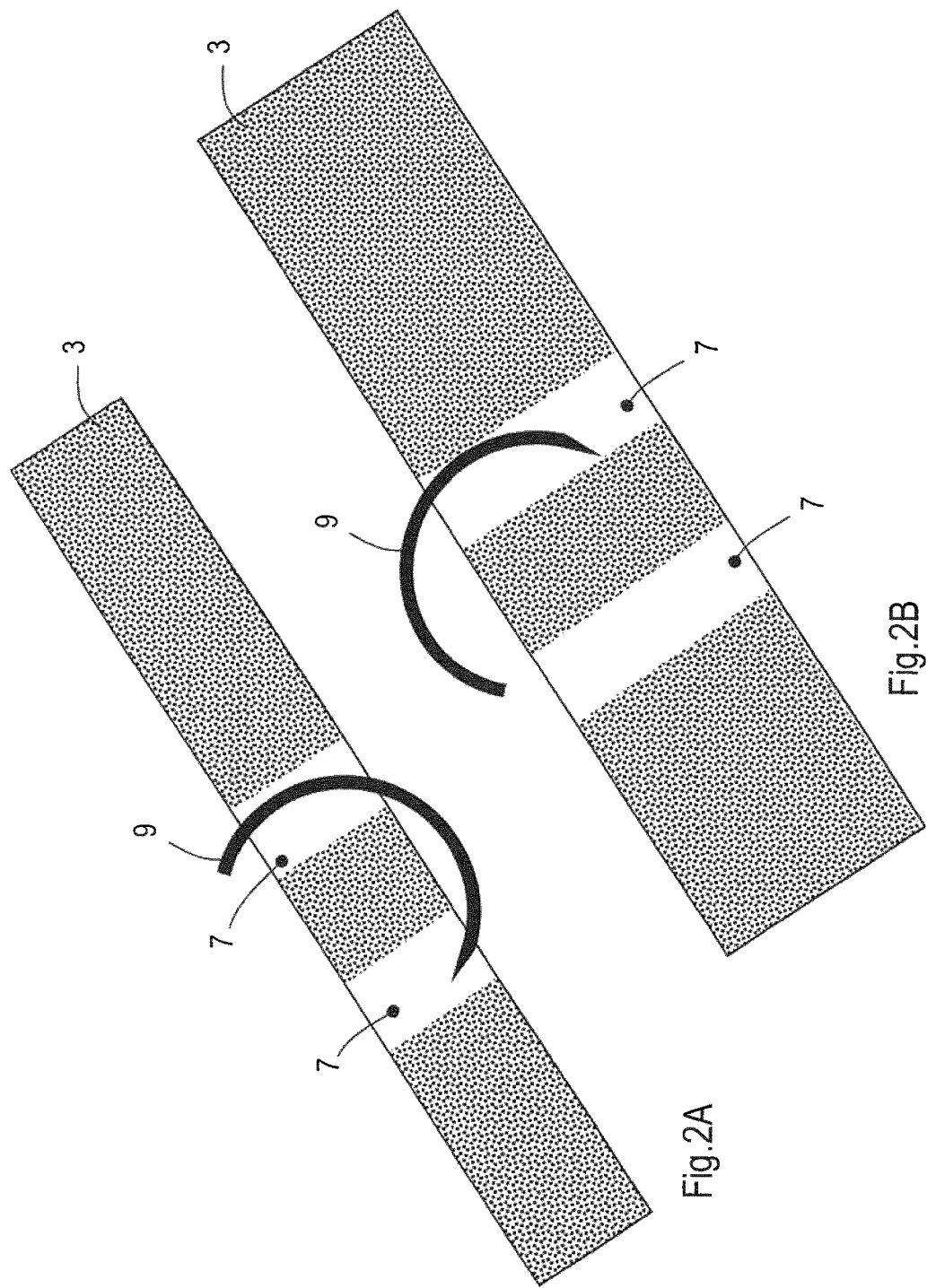

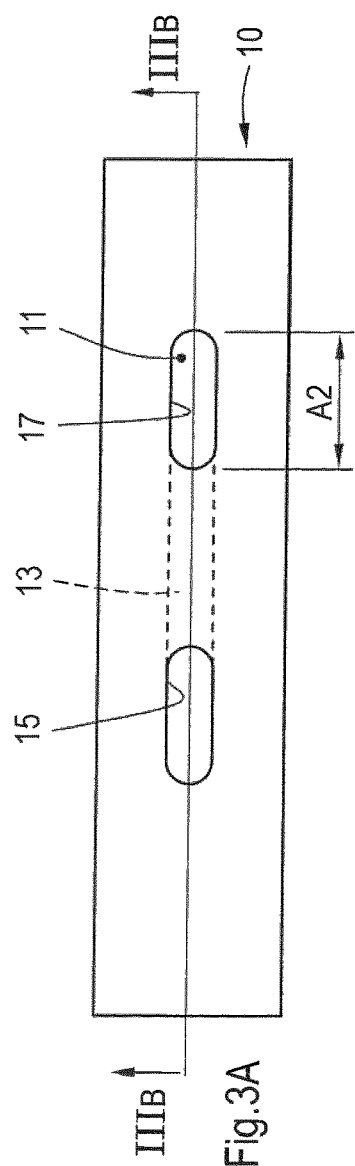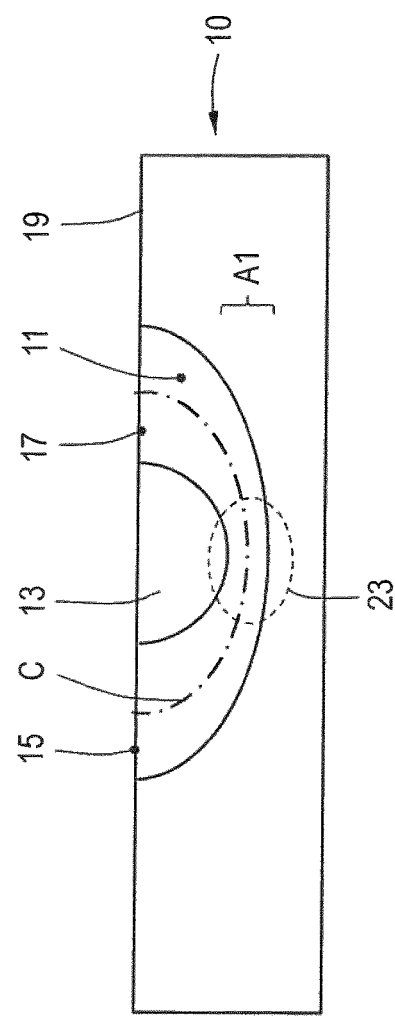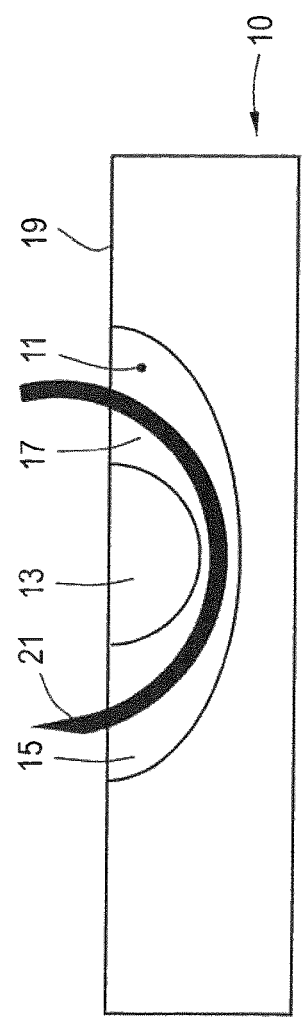

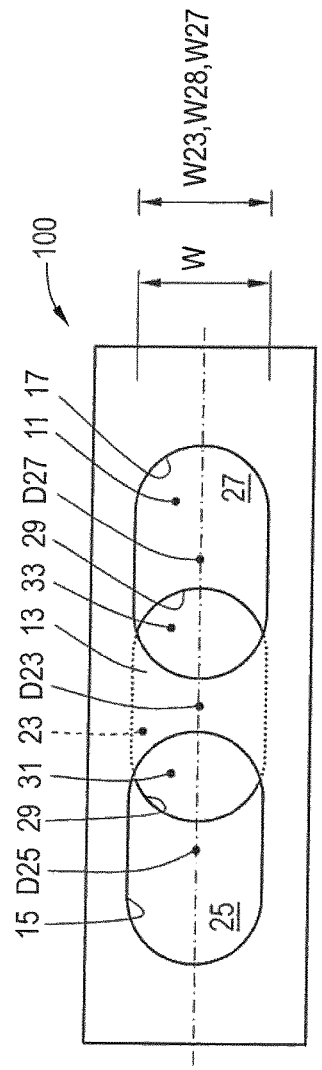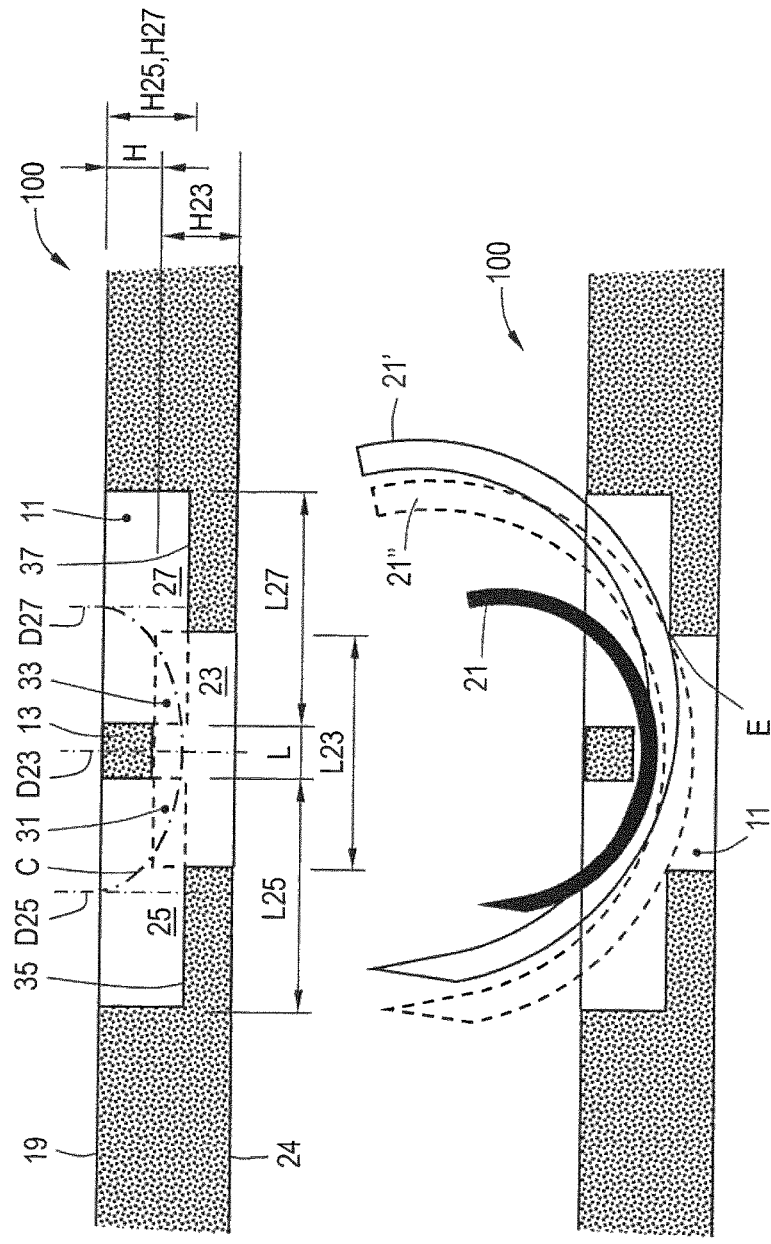
Fig.4A
Fig.4B
Fig.4C

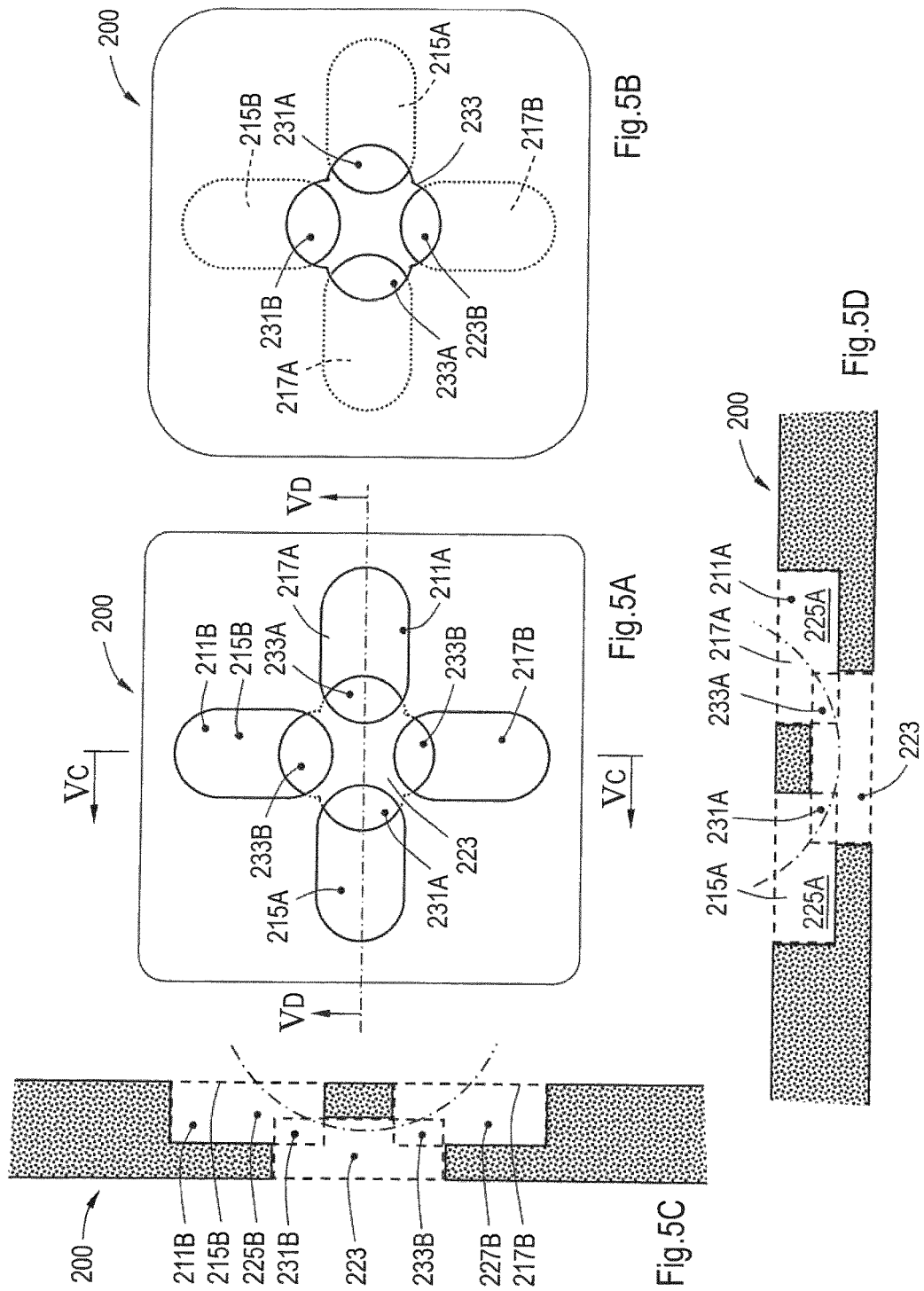

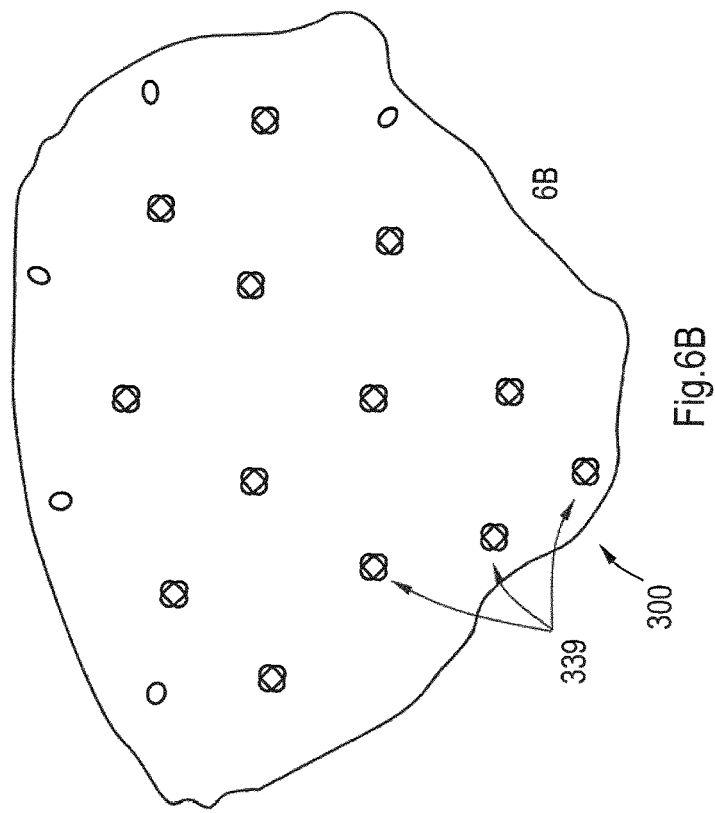
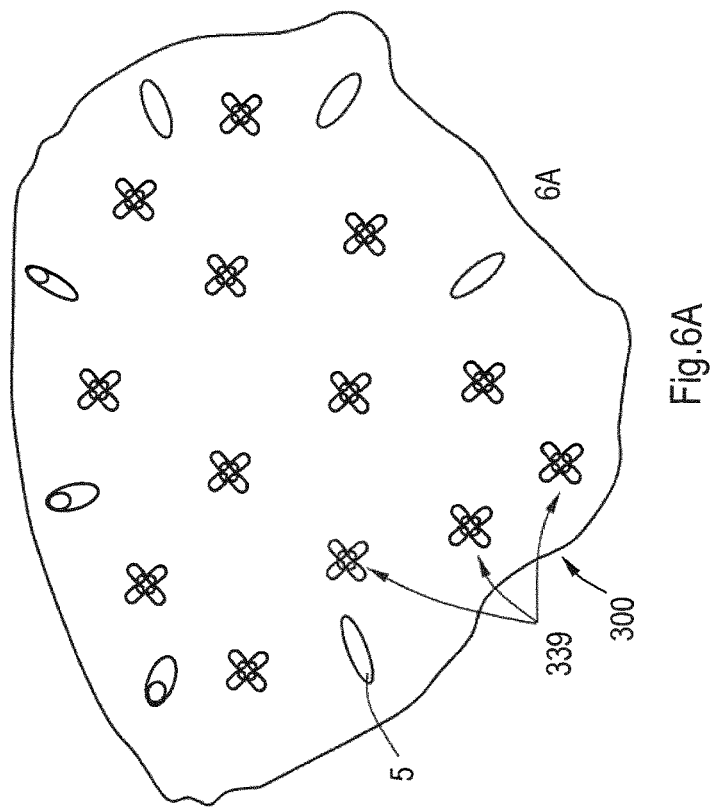

IMPLANT WITH SUTURE ANCHORS AND METHOD

CROSS-REFERENCE TO RELATED APPLICATION

The present application is a national stage filing of International patent application Serial No. PCT/EP2015/066468, filed Jul. 17, 2015, and published in English as WO 2016/012376 A1 the content of which is hereby incorporated by reference in its entirety.

TECHNICAL FIELD

The present disclosure relates to an implant, in particular a patient specific implant for replacing, augmenting and/or reconstructing a bone structure.

BACKGROUND

The discussion below is merely provided for general background information and is not intended to be used as an aid in determining the scope of the claimed subject matter.

The present disclosure relates to an implant, such as a cranial implant, for attachment to an edge of a defect in a bone structure and for attachment to soft tissue.

Such implants, which are sometimes referred to as patient specific implants (PSI), are employed for repairing defects in bone structures resulting from e.g. surgery or trauma, tumour and/or a birth defect. The implant may partially or fully close a defect, such as an opening in a skull, protect the tissue underneath, e.g. brain tissue, and/or correct and/or restore the contour of the bone structure. Such implants are generally custom made, preferably adhering to the ISO 13485 quality management standard for medical devices.

Implants may have different origins. For instance, autogenous grafts are taken from one part of a human or animal body and implanted in another part of that same body and allografts are bone grafts taken from an individual from a species and inserted in the body of another individual of that same species. Alloplastic implants are implants made from body foreign material.

All implants have in common that they must be securely fixed to the bone structure. Further, soft tissue in some cases must be securely attached to the implant. Various techniques have been applied in the past for attachment of soft tissue to implants or bone. These can generally be divided in bone plates, suture anchors and stapling techniques.

However, bone plates and suture anchors must be fixed themselves to the bone or implant and they require introduction of significantly more foreign material into the body than the sutures themselves. This is undesired.

Bone boring devices are complex and expensive devices. They require a large operating space and require significant forces for penetrating the bone structure to apply the suture, which may reside quite shallowly in the bone structure. Due to the materials used for allografts, the devices tend not to be suitable for use with other material than natural bone.

Consequently, there is a desire for improvements.

SUMMARY

The Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

In an aspect an implant for repairing a defect in a bone structure is provided, e.g. a patient specific implant which may replace, augment and/or reconstruct a bone structure. The implant comprises a U-shaped suture channel which extends along a center line through the implant, e.g. underneath a bridge portion spanning and defining a portion of the suture channel, and which has first and second end openings opposite each other opening to a common face. The suture channel has a middle portion with a first size in cross section with respect to the center line of the suture channel and at least one of the end openings, preferably both opposite end openings, has a second size in cross section with respect to the center line of the suture channel larger than the first size, in particular having a length in at least one direction in cross section with respect to the center line of the channel that is larger than the largest of length, width and height of the bridge, for guiding curved suture needles through the channel.

A bridge portion may define at least part of the channel, of which at least part is fully enclosed. By opening to the common face, suturing of soft tissue and/or other objects to the common face of the implant is facilitated. Having an opening size larger than the middle portion facilitates insertion and guiding of the needle into and through the channel. In particular, curved suture needles of different sizes, in particular of different radii of curvatures can be facilitated, increasing flexibility of use of the implant.

In another aspect an implant for repairing a defect in a bone structure is provided, e.g. a patient specific implant which may replace a bone structure. The implant comprises a U-shaped suture channel which extends along a center line through the implant, e.g. underneath a bridge portion spanning and defining a portion of the suture channel, and which has first and second end openings opposite each other opening to a common face. The first end opening of the U-shaped suture channel is formed by a first hole extending into the implant from the common face in a first direction of extension and the opposite second end opening is formed by a second hole extending into the implant from the common face in a second direction of extension, the first hole and the second hole communicating within the implant and providing the U-shaped suture channel through the implant, for guiding curved suture needles through the suture channel.

A bridge portion may define at least part of the channel, of which at least part is fully enclosed. By opening to the common face, suturing of soft tissue and/or other objects to the common face of the implant is facilitated. By the arrangement of two communicating holes manufacturing of the implant is facilitated and may be done cost efficiently, e.g. with cutting and machining techniques.

Such implant may comprise a third hole extending into the implant in a third direction of extension and connecting the first and second holes to provide the U-shaped suture channel. Thus, the first and second holes need not themselves directly overlap and provide the communication. This facilitates providing the channel with different first and second and/or third directions of extension, different sizes, depths and/or diameters, increasing design freedom.

Embodiments may comprise a further opening arranged between the end openings at another face of the implant and/or a channel portion connecting the U-shaped channel with another face of the implant, e.g. an opposite face to the common face. Such channel portion may facilitate passing an object, e.g. a suture, through the implant from one side to another. E.g., the third hole of the embodiment described previously may extend from an opposite side.

An aspect comprises an implant for repairing a defect in a bone structure, e.g. a patient specific implant which may replace a bone structure, wherein the implant comprises a U-shaped suture channel which extends along a center line through the implant wherein at least one of the first and second end openings comprises a blind portion having a bottom wall portion facing towards the common face. This facilitates suturing by restricting an insertion depth of a needle, in particular a curved needle and also in particular if the blind wall is parallel to or being within about 30 degrees parallel to the common plane at the respective first or second opening. A bend or an edge of the blind bottom wall yielding to a relatively deep portion of the channel from the common plane towards the opposite end opening along the center line, in particular an edge of less than about 120 degrees, e.g. 90 degrees or acute, may provide a fulcrum for directing a curved needle underneath the bridge and through the channel.

A particular embodiment may comprise that the first and second holes extend from the common face and the third hole extends from an opposite face, the first to third holes being mutually offset but overlapping and at least pairwise connecting, together forming the U-shaped suture channel. The first to third directions may be parallel to each other and in such case they may lie in a common plane. This facilitates manufacturing of the implant. The overlapping portions of the first and third hole and of the third and second hole may form passages through the implant to a face opposite the common face.

An embodiment may comprise a second U-shaped suture channel portion extending along a second center line through the implant from the first end opening to the second end opening, providing two adjacent channels between the same end openings, or to a third end opening also opening to the common face. This increases flexibility for positioning sutures. In such case, at least part of a bridge portion may be common to and span both U-shaped channels, e.g. in a Y-shaped arrangement of channels sharing a common bridge over the interconnection of the respective channel portions in the "legs" of the Y-shape.

In another such case, the further U-shape suture channel may extend next to each other.

An embodiment may comprise an additional U-shaped suture channel portion which extends along an additional center line through the implant intersecting the aforementioned U-shaped suture channel and which has opposite additional first and second end openings opening to the common face. Thus, an X-crossing arrangement of U-shaped channels may be provided which increases flexibility of use.

Embodiments may comprise that at least one of the first and second openings has an elongated cross sectional shape with respect to the center line and/or direction of extension, respectively, with an aspect ratio of at least 1 to 1.25, preferably between 1 to 1.5 and 1 to 1.75 such as 1 to 1.6. However, higher ratios such as 1 to 2 or 1 to 2.5 may be provided. In such cases, guiding of a curved suture needle through the U-shaped channel may be provided for various radii of curvature of suture needles.

Embodiments may comprise that at least the first and second end openings form slots with their respective length directions parallel to each other, in particular both lengths extending in line with each other. The respective lengths may be adjacent, staggered, in-line and/or in-plane.

In a further aspect, a method of manufacturing an implant as described herein comprises the step of forming an implant for repairing a defect in a bone structure, in particular a patient-specific implant for attachment to an edge of the defect in a bone structure, the implant comprising an outer face and an inner face, the step of forming two holes from a common face into the implant and the step of forming at least one other hole from a face into the implant, the first to third holes providing the U-shaped suture channel. Such method allows manufacturing an implant with a large degree of design freedom, e.g. to adapt to patient-specific properties, and readily position a suitable suture channel in a desired position in the implant which facilitates suturing soft tissue to the implant.

In an embodiment, the method comprises forming two holes by cutting, e.g. drilling, machining, etc., into the implant from a common face and forming a hole by cutting into the implant from an opposite face, such that the three holes are offset but overlapping and connecting with each other. In such way manufacturing of the implant is further facilitated, and simultaneous formation of hole portions which extend through the implant from the common face to the opposite face may be provided, increasing flexibility of (use of) the implant.

Thus, herewith an implant is provided for attachment to soft tissue or other objects by suturing, wherein a suture may be anchored to the implant and may be laced through the suture channel through the implant from the common face using a desired curved suturing needle.

By forming the channel into and of the (material of) the implant, the implant requires no foreign bodies. This increases predictability, strength and robustness of the implant. By forming the channel with portions of increasing open size at or near the end openings in one major direction, e.g. providing slotted openings, flexibility for use with different sizes of suture needles is provided whereas strength and robustness of the implant are maintained and the outer shape of the implant is not significantly affected by the presence of the openings, compared to openings of similar cross sectional size in perpendicular directions, e.g. as formed by square or round holes. Hence, the implant may be less conspicuous when located underneath a thin layer of skin.

BRIEF DESCRIPTION OF THE DRAWINGS

The above-described aspects will hereafter be more explained with further details and benefits with reference to the drawings showing an embodiment of the invention by way of example.

FIGS. 2A-2B are examples of a curved suture needle in a traditional suture hole;

FIGS. 3A-3C show an embodiment of an implant with a suture channel as provided herein, in top view and cross section view, respectively, as indicated;

FIGS. 4A-4B show another embodiment of an implant with a suture channel as provided herein, in top view and cross section view, respectively, as indicated; FIG. 4C is a view as 4B with different curved suture needles;

FIGS. 5A-5D show another embodiment of an implant with a suture channel as provided herein, in top view, bottom view and, respectively, cross section views as indicated;

FIGS. 6A-6B show a top view and a bottom view of an embodiment realised as a patient specific cranial implant;

DETAILED DESCRIPTION OF EMBODIMENTS

Figure 1:
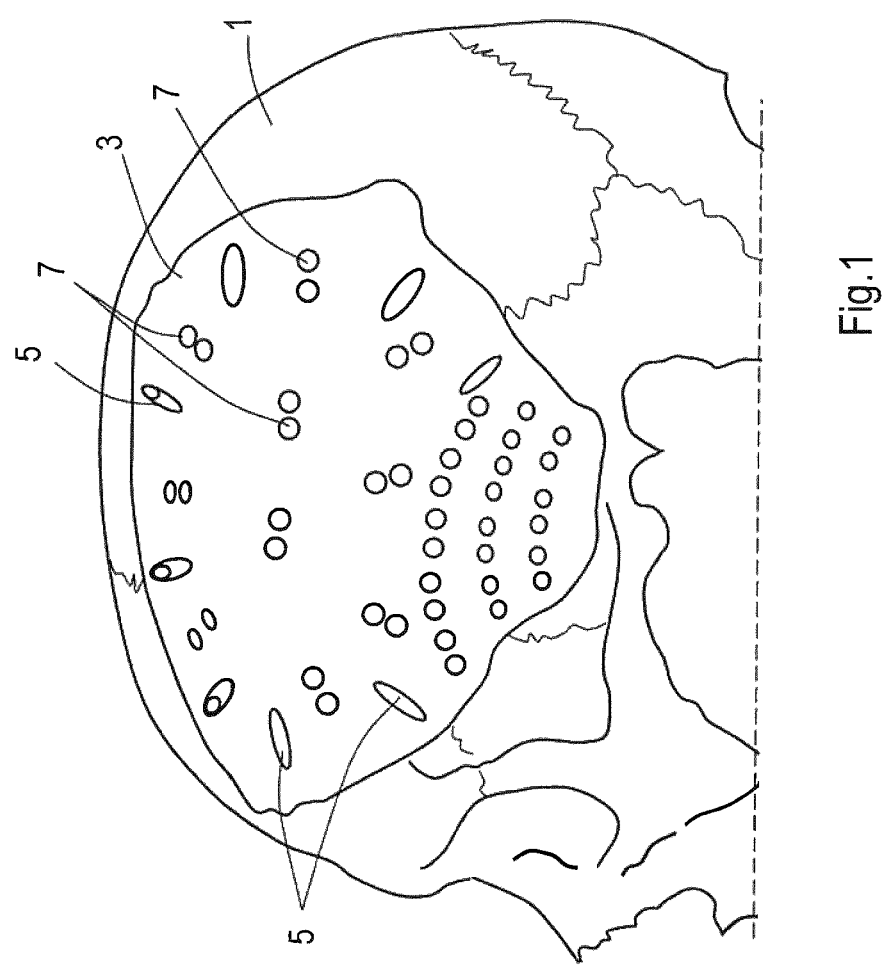
FIG. 1 is an example of a skull with a patient specific cranial implant in a bone defect.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral.

FIG. 1 shows a portion of a bone structure, here a human skull 1, having a defect resulting from surgery or trauma, which defect is closed by means of a cranial implant 3. The skull 1 and the implant 3 are generally biconvex, being curved along two substantially perpendicular directions of extension. Preferably the shapes of the bone structure 1 and the implant 3 are such that a substantially continuous structure is formed. Such implant allows reconstructing the anatomic shape of the intact bone structure. Some other examples of curved bone structures which may be provided with a curved implant are a rib, a shoulder blade, a pelvis.

The implant 3 is attached to the skull 1 via tangential fastenings 5 in a manner known in itself from EP 2 480 170, but other attachment methods may also be used. The implant may be made of a metal, for instance medical grade titanium. Alternative materials include, but are not limited to, polymers, e.g. polymethyl(meth)acrylate (PM(M)A), polyether ether ketone (PEEK), polyether ketone ketone (PEKK), and ceramic materials, e.g. calcium phosphate, hydroxy-apatite, zirconium oxide or aluminium oxide. A non-metallic implant 3 tends to remain closer to the local body temperature of the patient than a metallic implant 3, improving comfort and reducing complications. The implant 3 can be closely matched to a desired shape and/or to the shape of an edge of the defect in the bone structure 1 by means of CT-scans and 3D modelling, in a manner known in itself, such that a pre-operatively fabricated implant may be employed. Suitable manufacturing techniques comprise cutting techniques, such as machining, milling, turning, and/or additive manufacturing techniques such as "3D-printing". Different elements may be assembled to a single implant.

The implant 3 comprises several holes 7 through the implant 3, which may be used to attach soft tissue to the implant, e.g. muscle tissue, skin tissue and/or the meninges.

FIGS. 2A-2B show exemplary cross sections through a portion of an implant 3, having holes 7, and further showing a curved suture needle 9 as commonly known. Since an implant replacing a bone structure may be several millimeters to centimeters thick, a curved suture needle 9 extends below the implant and may damage underlying tissue (FIG. 2A), or may not be able to pass through the implant 3 as indicated in FIG. 2B. Surgeons therefore have to use significant care and/or rely on other means for attaching sutures which is often undesired as set out before.

FIGS. 3A-3B are a top and cross section view, respectively, of a portion of an implant 10 as provided herewith. The implant 10 comprises a U-shaped suture channel 11 which extends along a center line C through the implant 10 underneath a bridge portion 13 spanning and defining a portion of the suture channel 11. The suture channel 11 has opposite first and second end openings 15, 17, opening to a common face 19, e.g. an outer face of the implant 10. FIG. 3C is the view of FIG. 3B but showing an exemplary semi-circular suture needle 21 passing through the suture channel. The U-shaped suture channel 11 has a middle portion 23 underneath the bridge 13 with round shape having a diameter of first size A1 in cross section with respect to the center line C of the suture channel 11. The cross sectional size of the channel increases in size towards the end openings 15, 17 of the suture channel, here, the cross sectional shape gradually varies from about circular to elongated at the end openings 15, 17, having a size A2. Here the channel has a substantially constant width perpendicular to the plane containing the center line C. Due to the varying cross sectional size and shape, suture needles of different radii of curvature may be passed through the channel for a given depth of the channel with respect to the common face 19. Due to the formation of the channel 11 towards and at the end openings 15, 17 as slotted portions, in particular being parallel and more in particular being in line, suture needles 21 of different curvatures are similarly and strongly guided in directions perpendicular to a plane comprising (the center line C of) the U-shape of the channel 11. The larger the difference between the first and second sizes A1, A2, the larger the variation in curvatures of suture needles that can be accommodated through the channel 11.

FIGS. 4A-4B are a top and cross section view, respectively, of a portion of another embodiment of an implant 100 as provided herewith. FIG. 4C is the view of FIG. 4B but indicating suture needles 21, 21' and 21". As before, the implant 100 also comprises a generally U-shaped suture channel 11 which extends along a center line C through the implant 10 underneath a bridge portion 13 spanning and defining a portion of the suture channel 11. The suture channel 11 has opposite first and second end openings 15, 17, opening to a common face 19.

The bridge 13 has a center width W, a length L and a height H. Here, both opposite end openings 17, 19, have a size in at least one direction (here lengths L15 and L17, respectively) in cross section with respect to the center line of the suture channel larger than the largest of length, width and height of the bridge (here width W is the largest), for easier guiding curved suture needles through the suture channel 11.

A further channel portion 23 extends from the U-shaped channel 11 through the implant 100 to a second face 24 of the implant 100 which here is opposite the common face 19, e.g. forming an outer face 19 and an inner face 24. Here, the first end opening 15 of the U-shaped suture channel is formed by a first hole 25 extending into the implant 100 from the common face 19 in a first direction of extension D25 and the second end opening 17 is formed by a second hole 27 extending into the implant 100 from the common face 19 in a second direction of extension D27. The further channel section 23 is formed by a third hole 23 extending into the implant 100 from the second face 24 in a third direction of extension D23 providing a third opening 29 to the implant 100. The first, second and third holes 25, 27, 23 are offset from each other. The (lumina of) the first, second and third holes 25, 27, 23 coincide at volumina 31, 33 so that the first hole 25 and the second hole 27 communicate, through the third hole 23, within the implant 100, providing the desired U-shaped suture channel 11 through the implant 100 for guiding curved suture needles 21, 21', 21" of different radii of curvature and/or different thickness through the suture channel 11, as shown in FIG. 4C.

In the shown implant 100 the first, second and third directions of extension D25, D27, D23 are chosen to be parallel and even in one plane, although neither option is essential. The shown exemplary first, second and third holes 25, 27, 23 are slotted holes with their lengths L25, L27, L23 larger than their (as it happens: equal) widths W25, W27, W23 relative to the respective direction of extension D25, D27, D23, wherein the directions of elongation are chosen to be parallel to each other and even in line with another, although none of these options is essential. E.g., the holes may have sizes of Width 2.5 mm and Length 4 mm, resulting in an aspect ratio width:length of 1:1.6. Other exemplary sizes may be L=3 mm, L25=4 mm, L27=4 mm, L23=6 mm, H=1 mm, H25=1.75 mm, H27=1.75 mm. However, none of these values are essential and a wide range of sizes may be suitably employed.

Inter alia due to the offset arrangement of the first, second and third holes 25, 27, 23, each of the first and second holes 25, 27 is provided with a blind portion realised by a bottom wall portion 35, 37 facing towards the common face 19. The bottom wall portions 35, 37 are positioned lower than the bottom side of the bridge portion 13 with respect to the common face 19. The bottom wall portions 35, 37 provide an edge E to the third hole 23, which may be used as a fulcrum for pivoting and/or guiding a suture needle (compare 21' and 21" in FIG. 4C), which facilitates passing the suture needle through the channel 11 and reduces chances of damaging the implant 100 and/or a sharp tip of the needle 21 by hitting the tip into a wall of the channel 11.

Inter alia due to the slotted shape of the holes 25, 27, longer than the depths H25, H27 of the first and second holes 25, 27 into (the material of) the implant 100, the cross sectional size of the channel 11 increases from a middle portion underneath the bridge 13 towards the end openings 15, 17, which facilitates use with suture needles 21 of different radii of curvature.

Due to inter alia the channel portion provided by the third hole 23 an object, e.g. such as a (possibly straight) needle, a drain, a probe, a suture, etc. may be passed through the implant 100. Since (the lumen of) the third hole 23 extends beyond the bridge 13 it is visible from the common face 19 adjacent the bridge portion 13 (FIG. 4A) and access to it through the volumina 31 and/or 33 is facilitated. E.g., in case the implant 100 is a cranial implant, the meninges may be sutured to the implant 100. Further, due to the third hole 23 chances of damaging the implant and/or a sharp tip of a curved needle 21 by hitting the tip into a wall of the channel 11 are reduced.

The shape of provided by the shown hole geometry allows suturing after placing the implant, instead of having to arrange sutures in and/or through the implant before placement. The risk of damaging the underlying tissue by accident is reduced. Furthermore, these holes can prevent pressure build-up underneath the implant. The holes described here allow for a wide variety of needle sizes. Also, the needle can be used to suture from outside to outside (through the channel) but also from inside to outside and the other way around.

FIGS. 5A-5D show an embodiment of an implant 200, comprising a first U-shaped suture channel 211A arranged in a first direction and in addition a second U-shaped channel 211B perpendicular to the first U-shaped channel 211A intersecting the U-shaped suture channel 211A. In this embodiment, each of the U-shaped suture channels 211A, 211B is formed equal and just as the U-shaped channel 11 of FIGS. 4A-4C, having opposite first and second end openings 215A, 217A and, respectively an additional first end opening 215B and an additional second end opening 217B, all opening to the common face 221 and all formed by respective holes 225A, 225B, 227A, 227B. All holes are communicating because of a common hole 223 extending into the implant from the opposite face, coinciding with the respective holes 225A, 225B, 227A, 227B in volumina 231A, 233A, 231B, 233B. Thus, two crossing, intersecting U-shaped suture channels are formed, sharing a common bridge portion 213 here being located at the heart of the arrangement. In addition, all pairs of each adjacent holes 225A, 225B; 225B, 227A; 227A, 227B; 227B, 225A; are interconnected via the common hole 223 from the opposite face providing further respective U-shaped suture channels underneath the bridge portion 213, wherein the end openings 215A, 215B, 217A, 217B are slotted in cross section with respect to the respective center lines of each channel in a non-parallel direction, allowing use with different suture needle sizes, wherein the plane comprising the needle curvature may be oriented in a non-normal angle to the local shape of the common face; recall that the implant may follow a natural biconvex shape e.g. as in a cranial implant.

FIGS. 6A and 6B show a cranial implant 300 like the implant 3 of FIG. 1, here however comprising a plurality of crossing U-shaped suture channel arrangements 339 as explained with respect to FIGS. 5A-5D. Thus, in plural locations, soft tissue and/or other objects may be easily attached to the implant through the channels. Attachment to the outer face (FIG. 6A) may readily be done with curved suture needles of various sizes and radii of curvature, e.g. according to a surgeons' preference and/or in accordance with (a property of) the tissue and/or object to be attached. Attachment to the inside may be done from the outside by suturing through the holes 223 in the back side, e.g. first attaching suturing threads to the interior tissue and then passing the suturing threads through the desired channel arrangements 339. Fastening may be done over, rather than under, the bridge portion 213. The crossing suturing channels facilitate also attaching a suture for an outside tissue portion from the outside at the same location, by passing the desired outside suture underneath the bridge 213.

Figure 7A:
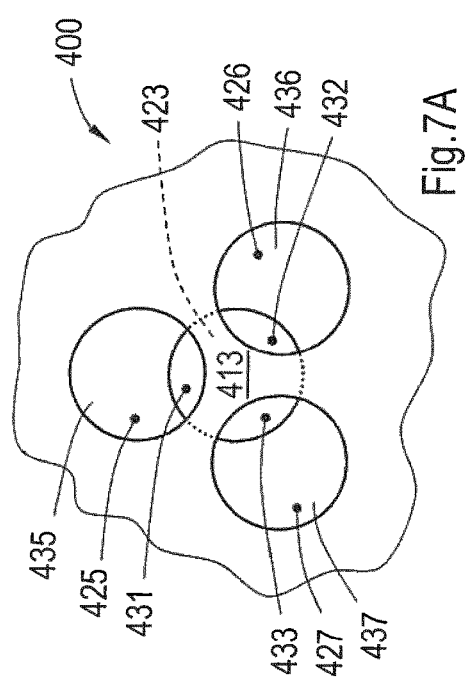
Figure 7B:
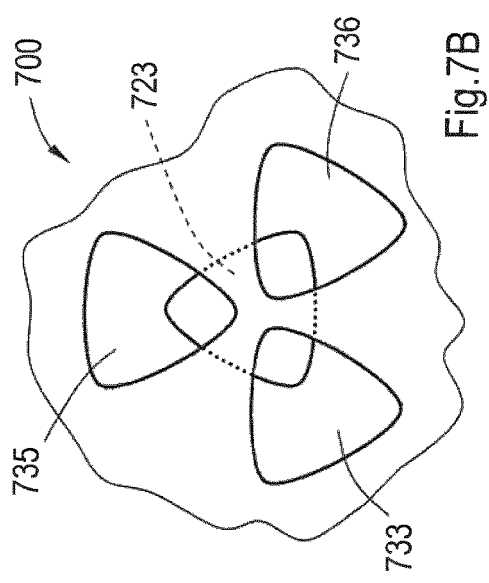

The invention is not restricted to the above described embodiments which can be varied in a number of ways within the scope of the claims. For instance FIG. 7A shows, similar to FIGS. 4A, and 5A, a top view of a portion of an implant embodiment 400, comprising an arrangement of three mutually offset holes 425, 426, 427 extending into the implant for a certain depth less than the implant thickness from a common face and a further hole 423 extending into the implant from an opposite face, overlapping and partly coinciding with the previously mentioned three mutually offset holes 425, 426, 427 with volumina 431, 432, 433. Thus, comparable to FIGS. 4A-6B, three U-shaped suture channels underneath a common bridge 413 spanning each channel, and three through connections through the implant are formed (through volumina 431, 432 and 433, respectively), each opening being safeguarded against accidental passing through by a blind bottom wall portion 435, 436, 437. To facilitate orienting a needle for each of the possible U-shaped suture channels, the holes 425, 426, 427 are formed round. The blind hole portions of the hole-based channels in this and other embodiments ensure that at least some implant material is present at the locations of the respective holes, and along at least most cross sectional planes through the channel(s), thereby fortifying the implant. Note that other hole shapes, e.g. such as generally triangular holes 725, 726, 727; 723 may be used as well as shown in an embodiment 700 in FIG. 7B. Further note that different holes may have different shapes and/or sizes.

Figure 8:
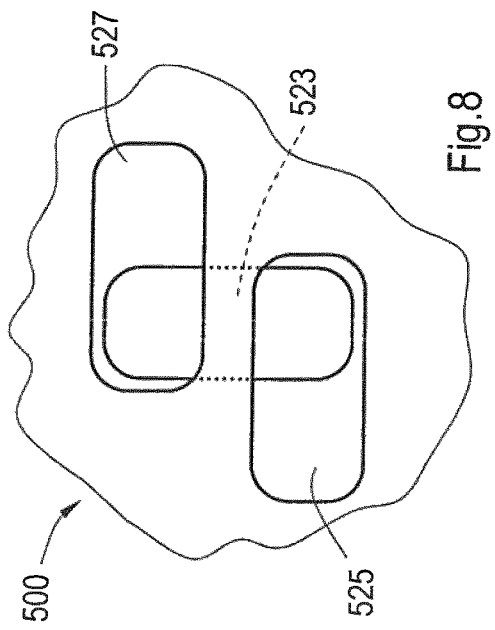
FIGS. 7A-9 show further embodiments of implants with suture channels as provided herein.

FIG. 8 shows a portion of an implant embodiment 500 comprising an arrangement of holes 525, 527 with a countersunk hole 523 like in FIGS. 4A-4C, and 7, here however the elongated holes 525, 527 being rotated with their longitudinal direction with respect to the embodiment of FIGS. 4A-4C into a general S-like shape. This enables the aforementioned benefits in a relatively differently shaped volume and prevents significant implant material removal in one plane. The implant may therefore be stronger at the location of the suture channel.

Figure 9:
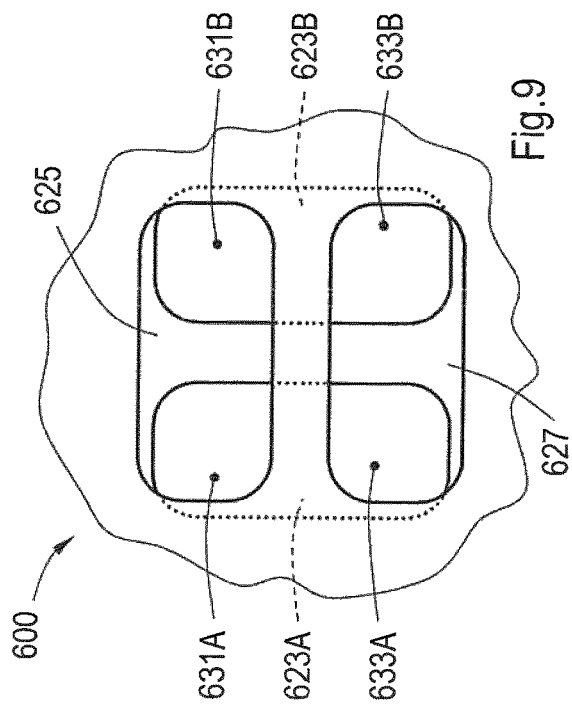

FIG. 9 shows a portion of an implant embodiment 600 comprising two holes 625, 627 opening to a common face and two countersunk holes 623A and 623B, respectively both connecting the holes 625, 627 at 631A and 633B, respectively, so that two adjacent U-shaped suture channel portions are provided, each extending along a respective center line through the implant from the first end opening to the second end opening provided by the holes 625, 627. Note that such adjacent channels need not be equal, e.g. not necessarily extending parallel and/or having a common depth and/or with within the implant.

Edges of holes and/or openings may be bevelled or chamfered to prevent sharp edges and/or transitions.

Elements and aspects discussed for or in relation with a particular embodiment may be suitably combined with elements and aspects of other embodiments, unless explicitly stated otherwise.

The invention claimed is:

1. An implant for repairing a defect in a bone structure, wherein the implant comprises a body having a least a pair of faces facing in opposite directions and a U-shaped suture channel which extends along a U-shaped center line through the implant and which has opposite first and second end openings opening to a common face of the pair of faces,
   wherein the suture channel has a middle portion with a first size in cross section with respect to the center line of the suture channel and at least one of the end openings, has a second size in cross section with respect to the center line of the suture channel larger than the first size, in particular having a length in at least one direction in cross section with respect to the center line of the suture channel larger than a largest of length, width and height of a bridge spanning and defining a portion of the suture channel, for guiding curved suture needles through the suture channel,
   wherein the first end opening of the U-shaped suture channel is formed by a first hole extending into the implant from the common face in a first direction of extension and the opposite second end opening is formed by a second hole extending into the implant from the common face in a second direction of extension, the first hole and the second hole communicating within the implant and providing the U-shaped suture channel through the implant, for guiding curved suture needles through the suture channel,
   wherein the implant comprises a third hole extending into the implant in a third direction of extension and connecting the first and second holes to provide the U-shaped suture channel,
   wherein the first and second holes extend from the common face and the third hole extends from an opposite face, the first to third holes being overlapping and at least pairwise connecting,
   wherein the first to third holes are mutually offset such that each of the first and second holes is provided with a blind portion realised by a bottom wall portion facing towards the common face.

2. The implant according to claim 1, wherein the blind portions are positioned lower than a bottom side of the bridge with respect to the common face.

3. The implant according to claim 1, wherein the bottom wall of the blind portion is parallel to or within about 30 degrees parallel to the common plane at the respective first or second opening.

4. The implant according to any claim 1, wherein a bend or an edge of the blind portion yielding to a relatively deep portion of the channel from the common face towards the opposite end opening along the center line, in particular an edge of less than about 120 degrees provides a fulcrum for directing a curved needle underneath the bridge and through the channel.

5. The implant according to claim 4 wherein the bend of the blind portion yielding to the relatively deep portion of the channel from the common face towards the opposite end opening along the center line is 90 degrees.

6. The implant according to claim 4 wherein the bend of the blind portion yielding to the relatively deep portion of the channel from the common face towards the opposite end opening along the center line is acute.

7. The implant according to claim 1, comprising a second U-shaped suture channel portion extending along a second center line through the implant from the first end opening to the second end opening or to a third end opening also opening to the common face.

8. The implant according to claim 1, comprising an additional U-shaped suture channel portion which extends along an additional center line through the implant intersecting the U-shaped suture channel and which has opposite additional first and second end openings opening to the common face.

9. The implant according to claim 1, wherein at least one of the first and second openings has an elongated cross sectional shape with respect to the center line.

10. The implant according to any claim 1, wherein at least the first and second end openings form slots with their respective lengths parallel to each other.

11. The implant according to claim 1, wherein both opposite end openings have the second size in cross section with respect to the center line of the suture channel larger than the first size.

12. The implant according to claim 11, wherein all first to third directions are parallel to each other in which case they may lie in a common plane.

13. The implant according to claim 1, wherein at least one of the first and second openings has an elongated cross sectional shape with respect to the center line and direction of extension, respectively, with an aspect ratio of at least 1:1.25.

14. The implant according to claim 1, wherein at least one of the first and second openings has an elongated cross sectional shape with respect to the center line and direction of extension, respectively, with an aspect ratio of at least 1:1.6.

15. The implant according to any claim 1, wherein at least the first and second end openings form slots with their respective lengths parallel to each other, wherein both lengths extending in line with each other.

16. An implant for repairing a defect in a bone structure, wherein the implant comprises a U-shaped suture channel which extends along a U-shaped center line through the implant and which has opposite first and second end openings opening to a common face,
   wherein the suture channel has an enclosed middle portion with a first size in cross section with respect to the center line of the suture channel and both opposite end openings have a respective second size in cross section with respect to the center line of the suture channel larger than the first size, in particular having length in at least one direction in cross section with respect to the center line of the suture channel larger than a largest of length, width and height of a bridge spanning and defining the middle portion of the suture channel, for guiding curved suture needles through the suture channel, wherein each of the first and second end openings comprises a blind portion having a bottom wall portion facing towards the common face and the cross sectional size of the channel increases in size from the middle portion towards both respective opposite first and second end openings.

17. The implant according to claim 16, wherein the U-shaped suture channel has the middle portion underneath the bridge with round shape having a diameter of the first size in cross section with respect to the center line of the suture channel.

18. The implant according to claim 17, wherein the cross sectional size of the channel increases in size towards the end openings of the suture channel.

19. The implant according to claim 18, wherein the cross sectional shape of the channel gradually varies from about circular to elongated at the end openings.

* * * * *